United States Patent [19]

Phillips et al.

[11] Patent Number: 4,760,850
[45] Date of Patent: Aug. 2, 1988

[54] METHOD FOR BALANCING ASSISTANCE

[75] Inventors: Chandler A. Phillips, Tipp City; Jerrold S. Petrofsky, Beavercreek, both of Ohio

[73] Assignee: Wright State University, Dayton, Ohio

[21] Appl. No.: 863,744

[22] Filed: May 15, 1986

[51] Int. Cl.$^4$ ............................................... A61B 5/10
[52] U.S. Cl. ............................................... 128/432 W
[58] Field of Search ............... 128/423 W, 782, 779, 128/774; 340/666, 667, 407

[56] References Cited

U.S. PATENT DOCUMENTS

| | | | |
|---|---|---|---|
| 3,791,375 | 2/1974 | Pfeiffer | 128/779 |
| 3,948,379 | 4/1976 | Warner | 128/24.1 |
| 4,004,290 | 1/1977 | Kobayashi et al. | 128/779 |
| 4,195,626 | 4/1980 | Schweizer | 128/774 |
| 4,387,472 | 6/1983 | Wilson | 128/779 |
| 4,554,430 | 11/1985 | Kress | 128/774 |
| 4,569,352 | 2/1986 | Petrofsky et al. | |
| 4,974,491 | 8/1976 | Sipe | 128/779 |

FOREIGN PATENT DOCUMENTS

| | | | |
|---|---|---|---|
| 136247 | 4/1985 | European Pat. Off. | 128/774 |
| 3416873 | 11/1985 | Fed. Rep. of Germany | 128/782 |
| 8601588 | 3/1986 | World Int. Prop. O. | 128/774 |
| 128643 | 4/1959 | U.S.S.R. | 128/779 |
| 862912 | 9/1981 | U.S.S.R. | 128/774 |

OTHER PUBLICATIONS

"Foot & Shoe Cover for Footfall Pattern Measurements", by O. Johns et al. Med. & Biol. Eng. & Comp. 1/79, vol. 7, pp. 94–96.
"Leg Load Warning System for the Orthopedically Handicapped", by D. Endicott et al.; Med. & Biol. Eng., May 1974, pp. 318–320.
"Programmed Six-Channel Electrical Stimulation for Complex Stimulation of Leg Muscles", by P. Strojnik et al.; IEEE Trans. on Biolmed. & Eng., vol. 26, No. 2, Feb. 1979, pp. 112–116.
"Limb Load Alarm Device for Partial Weight Bearing Walking Exercise" by Miyzaki et al; Med. & Biol. Eng. Comput. Sep. 1978, vol. 16, pp. 500–506.
"A Myoelectically-Controlled Prosthesis with Sensory Feedback", Shannon, Medical & Biological Engineering & Computing, Jan. 1979, pp. 73–80.
"Computer Controlled Walking in the Paralyzed Individual", Petrofsky et al., The Journal of Neurological and Orthopaedic Surgery, Jul. 1983, pp. 153–164.
"External Control of Rate, Recruitment, Synergy and Feedback in Paralyzed Extremities", Solomonow et al, Orthopedics, Jul. 1984, pp. 1161–1169.
"Computer Synthesized Walking an Application of Orthosis and Functional Electrical Stimulation (FES)", Petrofsky et al, The Journal of Neurological & Orthopaedic Medicine & Surgery, Oct. 1985, pp. 219–230.

Primary Examiner—William E. Kamm
Assistant Examiner—David Shay
Attorney, Agent, or Firm—Biebel, French & Nauman

[57] ABSTRACT

Method for assisting in the maintenance of a balanced stance by a person who has lost the sense of touch in one or both feet. Load signals are generated in correspondence with body weight loads applied at forward and rearward portions of the feet. The load signals are used for creation of tactile stimuli in a spaced pattern on a sensitive skin area of the person.

6 Claims, 4 Drawing Sheets

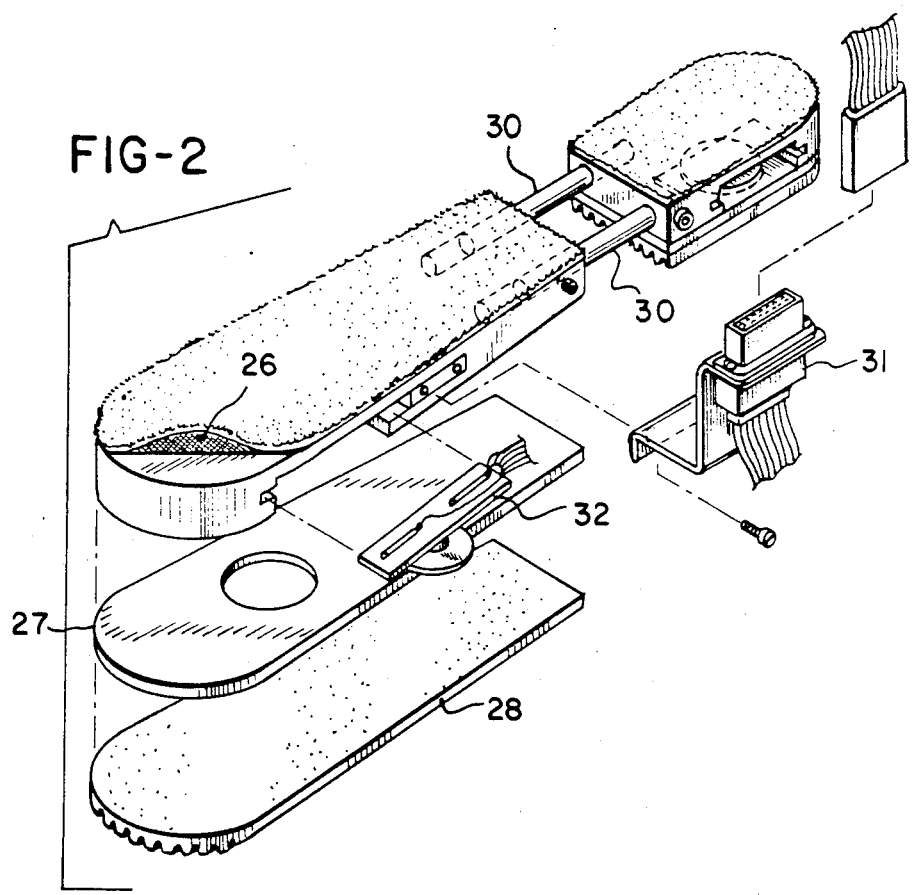
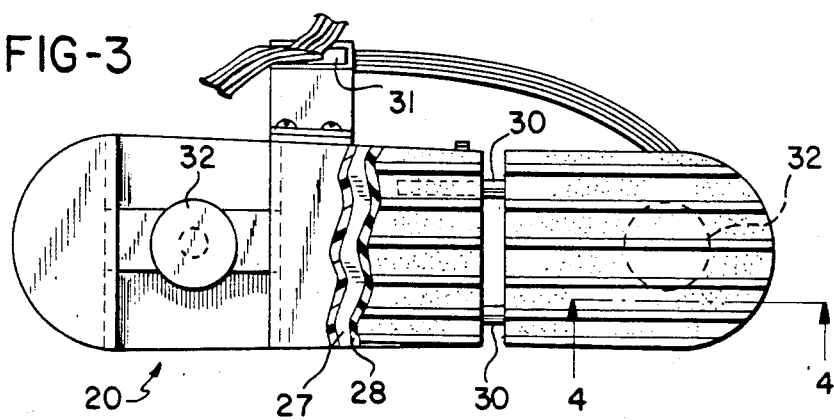

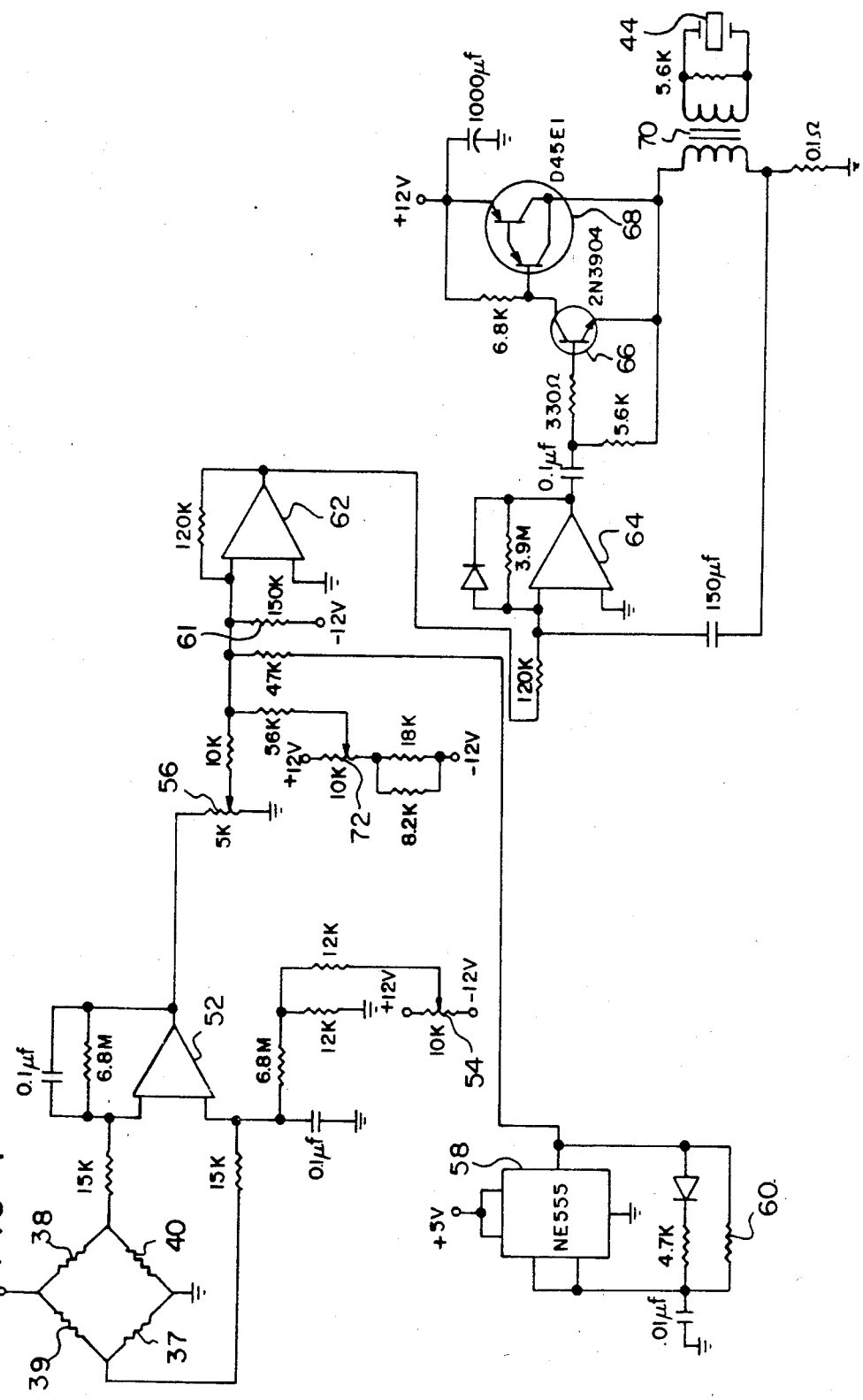

METHOD FOR BALANCING ASSISTANCE

BACKGROUND OF THE INVENTION

This invention relates to the field of balancing assistance for persons who are deprived of the sense of touch in one or both legs. Such deprivation may be due to the loss of a limb or may be the result of spinal cord injury. In either case the disabled person lacks information which is fundamental to the maintenance of vertical balance during standing or walking. Obviously the condition is much more severe for a person afflicted with spinal cord injury, because the damage affects both legs, as well as the entire body trunk below the level of the spinal cord injury. Thus, this invention is particularly applicable to the field of balancing assistance for spinal-cord-injured persons.

It is well known that a spinal cord injury breaks the communication link between the brain and the affected muscles, but the muscles themselves are otherwise undamaged. Thus, it has been found that useful movement of the muscles may be restored through functional electrical stimulation. Typical systems for performing such stimulation are disclosed in Petrofsky et al. U.S. Pat. No. 4,499,900 and in Petrofsky et al. U.S. Pat. No. 4,456,214, both of which deal with therapeutic exercise for leg muscles.

The systems disclosed in the above noted Petrofsky et al. patents include sensors which measure leg motion and feedback loops which are connected to a microprocessor. The microprocessor compares a measured movement to a desired movement and generates appropriate stimulation control signals. The stimulation control signals are applied to stimulation electrodes which are positioned for stimulating controlled contractions in target muscles.

Electrically stimulated walking is also feasible as disclosed in Petrofsky et al. U.S. Pat. No. 4,569,352. However, stimulated walking is a much more complex operation than simple stimulated leg exercising. As shown in Petrofsky et al. No. '352, stimulated walking may require coordinated, closed loop control of as many as ten muscle groups. Additionally, leg braces are required in order to avoid the necessity of stimulating even more muscle groups. The control problem is further complicated by the requirement to maintain a delicate vertical balance. The disabled person typically provides balancing control through the use of canes or a suitable walker. As taught in Petrofsky et al. No. '352, ON/OFF floor contact switches may be provided at the heels and toes of the disabled person. Information from these switches is provided to the microprocessor, but this does not contribute very much to balancing control.

It is also possible for a spinal cord injured person to achieve a certain degree of ambulation without functional electrical stimulation. This may be accomplished through use of a reciprocation-gait orthosis as disclosed in an article entitled "The LSU Reciprocation-Gait Orthosis" by Douglas et al., *Orthopedics* July, 1983, pages 834 through 839. This orthosis utilizes leg braces which are locked at the knees and hip joints which are interconnected by a pair of cables. Cable connections are made in such a fashion that extension of either hip produces flexion of the opposite hip. Balancing is achieved through a suitable walker.

A significant simplification of electrically stimulated walking may be achieved by combining stimulation with a reciprocation-gait orthosis, as described in a paper entitled "Computer Synthesized Walking, An Application of Orthosis and Functional Electrical Stimulation (FES)" by Petrofsky et al., *The Journal of Neurological & Orthopaedic Medicine & Surgery*, Vol. 6, Issue 3, October, 1985, pages 219 through 230. As with the other above described systems, a stable center of gravity must be maintained. Again, this is supplied by the disabled person through the use of canes or a walker.

In order for a human being to maintain an erect position during standing or walking it is necessary for the brain to receive some type of cognitive feedback. Heretofore the only cognitive feedback available to the spinal-cord-injured person has been provided by the sense of vision. Generally speaking the person looks down toward the floor, visually determines the sequence of walking and adjusts the upper body accordingly. Although this may be satisfactory in a controlled laboratory setting, it is not practical for routine walking in various environments. The visual sense of the person must be unrestricted for use in other activities.

Accordingly, there is a need to provide balancing assistance apparatus and method for use by persons who have been deprived of the sense of touch in one or both legs. Preferably, such apparatus and method should provide balancing information as cognitive feedback flowing directly to the disabled person without the intervention of a computer. Also, it is desirable that the balancing assistance operate in a stimulated or non-stimulated environment and function effectively both for walking and standing.

SUMMARY OF THE INVENTION

This invention provides balancing assistance for a person suffering a loss of the sense of touch in the lower extremities by supplying balancing information to a tactile interface above the point of injury. The required balancing information is generated by load transducers affixed to the bottoms of the feet. In the preferred embodiment a plurality of vibrocutaneous transducers are positioned in a predetermined pattern at the tactile interface. However, electrocutaneous stimulation is also feasible.

For the preferred embodiment utilizing vibrocutaneous transducers, there is provided on oscillator for generating an oscillating carrier signal. The carrier signal is amplitude modulated by the output from the load transducers. Preferably the carrier is generated at a frequency in a range between about 5 hz and 500 hz.

BRIEF DESCRIPTION OF THE DRAWING

FIG. 2 is an exploded perspective view of a foot plate unit.

FIG. 3 is a partially cut away bottom plan view of a foot plate unit.

FIG. 7 is an electrical schematic diagram.

DESCRIPTION OF THE PREFERRED EMBODIMENT

Figure 1:
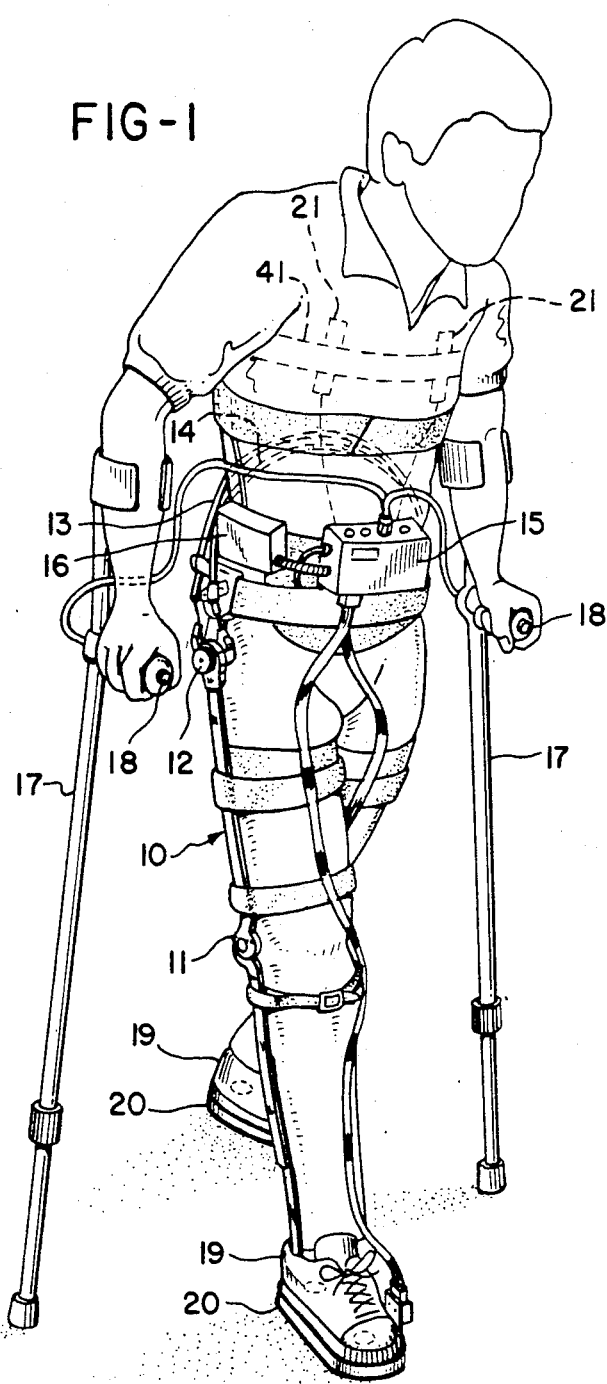
FIG. 1 is a pictorial illustration of a spinal cord injured person engaging in assisted walking.

Balancing apparatus in accordance with the present invention may be used for assisting stimulated walking, as generally illustrated in FIG. 1. The walking control system which forms no part of the present invention, comprises a pair of braces 10 equipped with knee joints 11 and hip joints 12 (only one knee joint 11 and one hip joint 12 being illustrated in the Figure). A pair of cables 13, 14 interconnect hip joints 12 in such a manner as to produce flexion of either hip in response to stimulated extension of the opposite hip. The disabled person achieves controlled alternating hip extension by alternating operation of a pair of control buttons 18, 18 mounted on canes 17, 17.

When control buttons 18, 18 are operated corresponding trigger signals are transmitted to an electronics package 15 which includes a suitably programmed computer. Power is supplied by a power package 16. Stimulated hip extension is produced by two sets of transcutaneous electrodes (not illustrated) connected to electronics package 15. The stimulation electrodes may be controlled in the manner generally taught in Petrofsky et al. U.S. Pat. No. 4,569,352 and may be incorporated within a tightly fitting garment as taught by Granek et al. U.S. Pat. No. 4,580,572. Reference may be made to the above mentioned paper published in The Journal of Neurological & Orthopaedic Medicine and Surgery for additional information regarding the operation of the stimulation control system.

Figure 4:
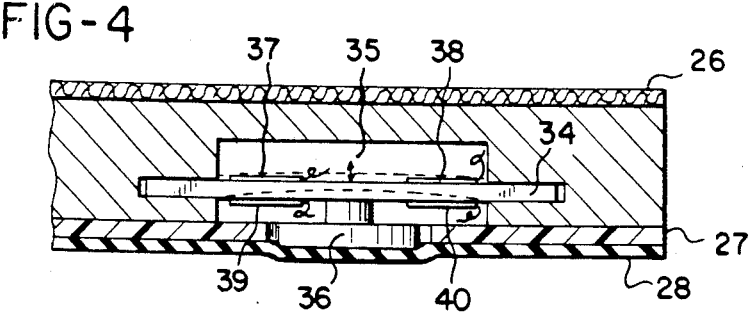
FIG. 4 is an enlarged cross sectional view taken along lines 4—4 of FIG. 3.

Balancing assistance for the disabled person is provided by a pair of foot plate units 20, 20 attached to the bottoms of the shoes 19, 19. Foot plate units 20, 20 generate load signals which are amplified and modulated by circuitry within the electronics package 15. This creates balance signal which are transmitted to tactile interface units 21, 21 positioned against the skin of the disabled person above the point of any spinal cord injury. Foot plate units 20, 20 each may include a pair of foot load transducers 32, 32 positioned at balance points near the ball and heel of the foot and configured as generally illustrated in FIGS. 3 and 4.

Figure 5:
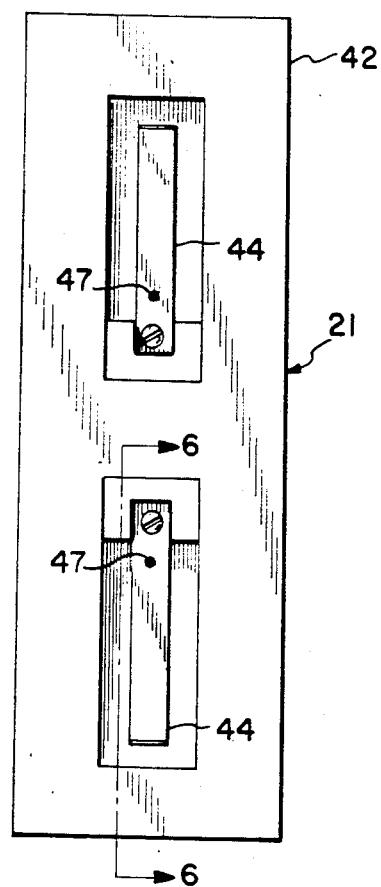
FIG. 5 is a rear elevation view of a tactile interface unit.
Figure 6:
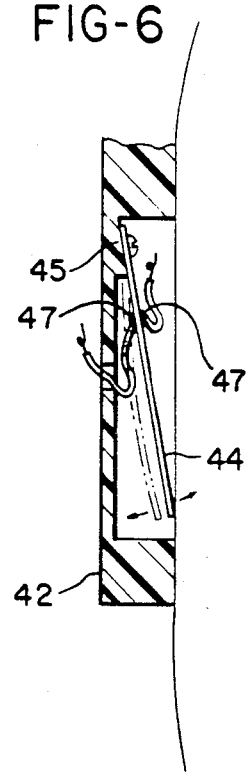
FIG. 6 is an enlarged cross sectional view taken along lines 6—6 of FIG. 5.

Each foot load transducer 32 generates control information for a corresponding receptor element 44 mounted within one of the tactile interface units 21, as illustrated generally in FIGS. 5 and 6. Preferably, receptor elements 44 comprise BIMORPH transducers which are caused to vibrate against the skin of the disabled person with a maximum amplitude which varies with the force being sensed by the corresponding foot load transducer 32. This provides four-point balancing information which may be readily interpreted by the disabled person and used for positioning canes 17, 17 and controlling upper body movements. The balancing information may also be used to assist in the timing of the operation of push buttons 18, 18.

Referring now to FIG. 2, a foot plate unit 20 may be covered by a cover 26 preferably comprising fastening material sold under the trademark VELCRO. A layer of cooperating fastening material may be applied to the lower surface of the mating shoe 19 so as to keep foot plate unit 20 mounted firmly in place. Foot plate unit 20 also comprises a support plate 27 and a sole 28. Sole 28 is preferably fabricated from a thin and relatively hard sheet of rubber material. This provides a non-skid surface and suitably covers foot load transducers 32, 32 without impairing the operation thereof. An electrical connector 31 may be mounted on the side of foot plate unit 20. The size of foot plate unit 20 may be adjusted through use of a pair of sliding rods 30, 30 as illustrated in FIG. 3.

A wide variety of different types of transducers may be employed for sensing the load at the balance points on the bottom of the foot plate unit 20. One suitable device, as illustrated in detail, in FIG. 4 may include a stainless steel flexure member 36 suspended within a cavity 35 in foot plate unit 20. A contact member 36 may extend downwardly from flexure member 34 to a point slightly below the lower plane of support plate 27. Sole 28 conformably covers contact member 36.

The foot load transducer 32 which is illustrated in FIG. 4 is positioned near the rear end of that foot plate unit 20 which is configured for attachment to the bottom of the right foot of the disabled person. Accordingly, when the disabled person begins to lean rearwardly, an increasing load is applied to contact member 36, thereby causing upward flexing of flexure member 34. This upward flexing is sensed by four strain gauges 37 through 40. These strain gauges may be of conventional design, each having a resistance in the order of about 350 ohms and a gauge factor in the order of about 2. They are applied to flexure member 34 in the customary manner and are electrically connected in a bridge arrangement, as illustrated in FIG. 7.

While a tactile interface unit 21 may support either electrocutaneous or vibrocutaneous receptor elements, the preferred embodiment utilizes vibrocutaneous elements 44, mounted as illustrated in FIGS. 5 and 6. They are preferably BIMORPH elements fabricated from G-1195 material. They are provided with nickel electrodes 47, 47 and are poled for series operation. BIMORPH elements 44, 44 are covered with an insulating material (not illustrated) which may a dental ceramic material. BIMORPH elements 44 are each cantilever mounted on an angled ledge 45 within a support frame 42, so that the distal end 46 projects beyond the plane of the skin contacting surface. This provides maximum tactile sensation.

As illustrated in FIG. 5, the two BIMORPH elements 44, 44 comprising one tactile interface unit 21 are cantilever mounted in opposite directions, so that their points of maximum vibration are separated by a vertical distance of about four inches. The two tactile interface units 21, 21 are mounted side by side in such a manner as to maintain a horizontal distance of about four inches between the BIMORPH elements in the two units. The tactile interface units may be maintained in position against the skin by means of a VELCRO (trademark) strap 41. It has been found that a human subject can readily discriminate among vibrating balance signals supplied at the corners of such a four inch square.

Each of BIMORPH elements 44 may be vibrated at a frequency ranging between about 5 Hz and 500 Hz, but a frequency of around 100 Hz is preferred. Acoustical damping material (not shown) may be used for dampening the sound produced by such vibration. Tactile descrimination may be improved by operating BIMORPH transducers 44 at slightly different frequencies. In one series of experiments frequencies of 70 Hz and 100 Hz were applied to BIMORPH elements constituting one tactile interface unit 21 with like frequencies being applied to the BIMORPH elements in the other tactile interface unit. In each case the amplitude of the vibration was modulated top and bottom using output signals from the rearward and forward foot load transducers respectively. Using such an arrangement it was found that a spinal cord injured person can maintain balance for a prolonged period of time when standing in a brace, even though blindfolded. However, balance was lost within about five seconds following deactivation of the tactile interface units.

As noted above, strain gauges 37 through 40 are mounted in a bridge arrangement. The output from this arrangement is a load signal which is applied to a differential amplifier 52 trimmed by a potentiometer 54. Strain gauges 37 through 40 are so configured (see FIG. 4 and FIG. 7) that when the bridge arrangement is subjected to strain, the output from differential amplifier 52 remains positive. The output from differential amplifier is applied via a gain adjusting potentiometer 56 to the input of a modulating amplifier 62. Modulating amplifier 62 also has inputs from a balance potentiometer 72 and from an oscillator in the form of an integrated circuit 58.

Integrated circuit 58 is an NE555 integrated circuit which produces an oscillating carrier signal comprising a series of 0.3 millisecond output pulses at a frequency depending upon the resistance of resistor 60. For generation of output pulses at a frequency of 70 Hz, resistor 60 may have a value of about 2 megohms. A resistance of about 1.33 megohms produces output pulses at a frequency of about 100 Hz.

Output signals from differential amplifier 52, balance potentiometer 72 and integrated circuit 58 are summed with the negative voltage across resistor 61 at the input of modulaton amplifier 62 and inverted. The output from modulation amplifier 62 is applied to inverting amplifier 64 for use in controlling the emittor-to-base current on transistor 66. Transistor 66 in turn controls the emittor-to-base current of Darlington amplifier 68. The output from Darlington amplifier 68 is applied to the primary winding of a 1:50 voltage step-up transformer 70, the secondary of which provides an energizing signal for application to a BIMORPH element 44.

The output signal from integrated circuit 58 has a square wave envelope varying between 0 and +5 volts. When summed with the negative voltage across resistor 61, this square wave envelope varies between −5 and 0 volts. The output signals from the strain gauge bridge and from balance potentiometer 72 apply a positive DC bias to this envelope. During the positive portion of this DC-biased envelope, the Darlington amplifier 68 conducts current and causes movement by BIMORPH element 44. The amplitude of that movement depends upon the amplitude of the positive portion of the DC-biased envelope which is applied to the input side of modulation amplifier 62. During the negative portion of the envelope, BIMORPH element 44 stops moving.

The circuitry of FIG. 7 is adjusted by having the disabled person place his weight equally on all four foot load transducers 32. Balance potentiometer 72 is then adjusted (so as to place a positive DC bias on the square wave) until the subject senses at all four BIMORPH elements 44 a level of vibration which is above threshold but yet relatively low and comfortable. This vibration level, hereinafter referred to as a reference level, varies from subject to subject. It will be seen then that increasing pressure on a foot load transducer 32 adds an additional positive DC offset to the square wave, thereby causing more current flow through Darlington amplifier 68 and a higher vibration amplitude at the corresponding BIMORPH element 44. Conversely, when the load on foot load transducer 32 decreases below that for which the balance adjustment was made, vibration of BIMORPH element 44 decreases below the reference level. If the load on the foot decreases sufficiently, vibration of BIMORPH element 44 will discontinue.

It will be appreciated that BIMORPH elements 44 may be replaced by other vibrocutaneous elements as well as by electrocutaneous elements. Thus, piezoelectric crystals could be used. Also, the output signals from the foot load transducers could be used for modulating either the frequency or the width of the pulses produced by the pulse wave generator. It should also be appreciated that the foot load transducers may be placed at the bottoms of artificial feet for providing balancing assistance to amputees.

While the form of apparatus herein described constitute a preferred embodiment of this invention, it is to be understood that the invention is not limited to this precise form of apparatus, and that changes may be made therein without departing from the scope of the invention which is defined in the appended claims.

What is claimed is:

1. Method of assisting a spinal-cord-injured person to maintain a balanced stance comprising the steps of:
   securing braces to both legs of said person,
   generating four balance signals corresponding to the loads created by the weight of said person at forward and rearward portions of both feet,
   applying tactile stimuli corresponding to said balance signals in a spaced pattern on a sensitive skin area of said person for enabling said person to maintain a balanced stance.

2. Method according to claim 1 wherein the step of applying includes applying said tactile stimuli at the corners of a square having sides approximately four inches long.

3. Method according to claim 2 wherein said stimuli are vibrational stimuli.

4. Method according to claim 1 wherein said balance signals includes the step of causing signals to oscillate at fixed frequencies in a range between about 5 Hz and 500 Hz and have peak amplitudes which vary in correspondence with variations in said loads; said tactile stimuli being generated by causing vibration of mechanical receptor elements in correspondence with variations in said balance signals.

5. Method according to claim 4 and comprising the further step of causing all of said stimuli to have relatively low and comfortable reference levels when said person has achieved a balanced stance.

6. Method according to claim 4 and comprising the further step of causing said stimuli to discontinue when their corresponding loads are reduced to zero.

* * * * *